United States Patent [19]

Adams

[11] 4,270,534

[45] Jun. 2, 1981

[54] FRANGIBLE VALVE ASSEMBLY FOR BLOOD BAGS AND THE LIKE

[75] Inventor: Elvis E. Adams, Downers Grove, Ill.

[73] Assignee: Baxter Travenol Laboratories, Inc., Deerfield, Ill.

[21] Appl. No.: 64,952

[22] Filed: Aug. 8, 1979

[51] Int. Cl.³ .............................................. A61M 5/00
[52] U.S. Cl. ............................. 128/214 D; 128/214.2; 128/247; 137/68 R; 251/342
[58] Field of Search ............. 137/68 R, 797; 251/342; 128/214 R, 214 D, 214.2, 247, 272; 150/8

[56] References Cited

U.S. PATENT DOCUMENTS

| | | | |
|---|---|---|---|
| 3,482,572 | 12/1969 | Grosclaude et al. | 128/214 D |
| 3,685,795 | 8/1972 | Caster | 251/342 |
| 4,181,140 | 1/1980 | Bayham | 137/68 R |

FOREIGN PATENT DOCUMENTS

| | | | |
|---|---|---|---|
| 49-10156 | 11/1974 | Japan | 137/68 R |
| 402286 | 5/1966 | Switzerland | 128/214 D |
| 497181 | 11/1970 | Switzerland | 137/68 R |

*Primary Examiner*—Robert G. Nilson
*Attorney, Agent, or Firm*—Paul C. Flattery; John A. Caruso; Q. Todd Dickinson

[57] ABSTRACT

Frangible valve means within a flexible tube. The valve means comprises a tubular portion having closed ends, and an elongated, generally rigid member carried on the exterior of the closed end and positioned within the flexible tube. Frangible means are provided to permit the opening of the tubular portion adjacent the closed end by rupture of an area of weakness by manual manipulation of the elongated member from outside of the flexible tube. In accordance with this invention, the flexible tube defines an inner end flange, while the tubular end portion of the valve means defines, at its end opposite to the closed end, a retention flange. The retention flange includes a cylindrical wall positioned generally coaxially to the tube and surrounding the periphery of the inner end flange. The cylindrical wall, in turn, carries an annular closure flange enclosing and retaining the inner end flange. A method of assembling the above structure is also disclosed.

4 Claims, 5 Drawing Figures

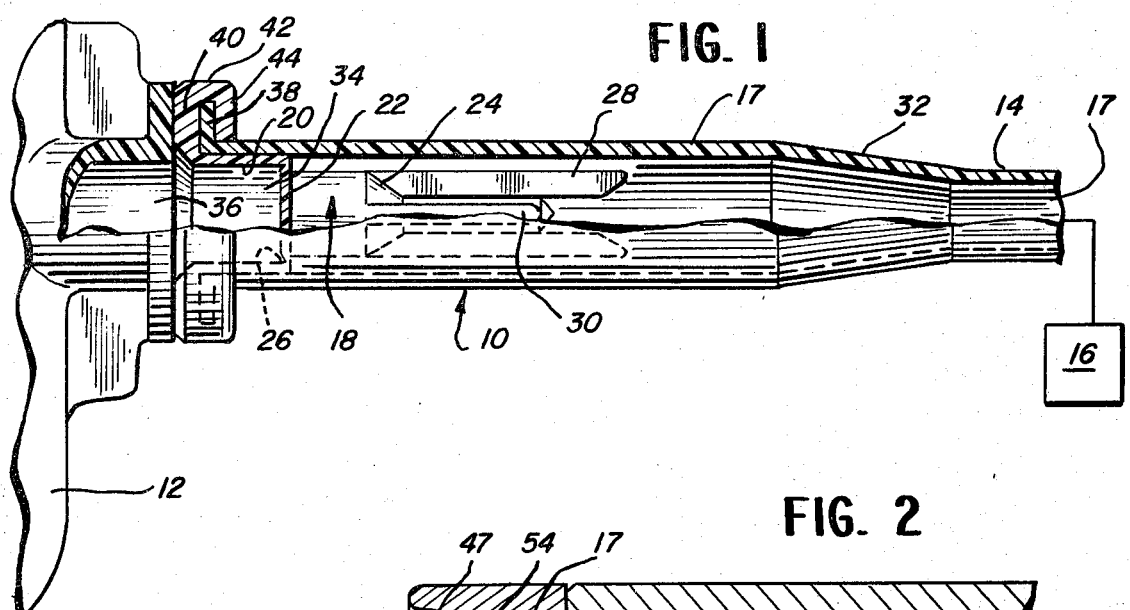
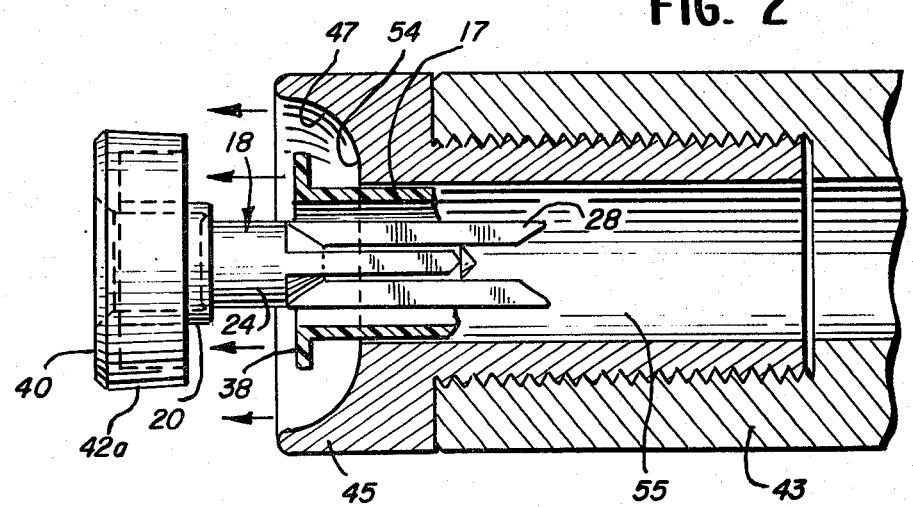
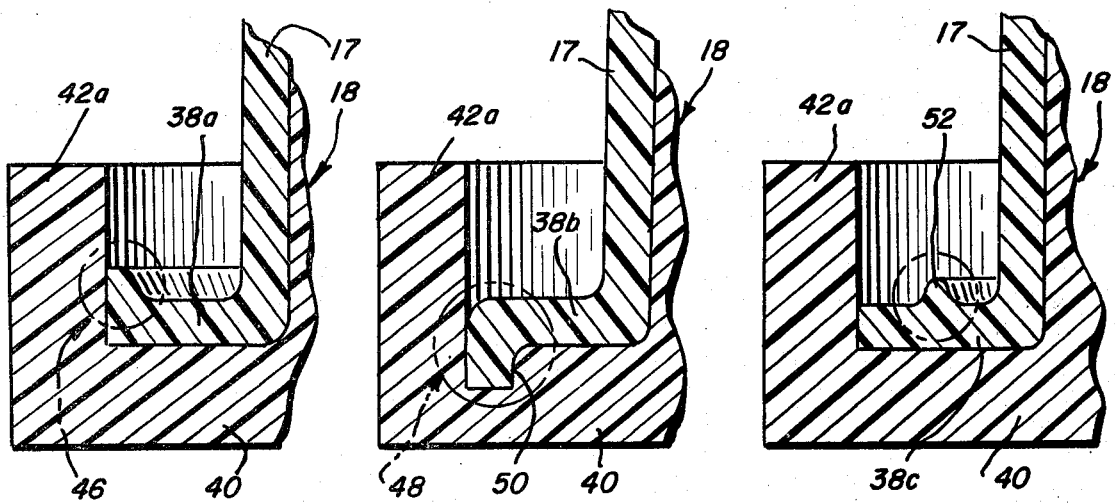

4,270,534

FRANGIBLE VALVE ASSEMBLY FOR BLOOD BAGS AND THE LIKE

BACKGROUND OF THE INVENTION

In U.S. application Ser. No. 876,790 of Edward L. Bayham, et al., filed Feb. 10, 1978, now U.S. Pat. No. 4,181,140, and Carter, et al. U.S. application Ser. No. 015,395, filed Feb. 26, 1979, frangible closures for flexible tubes are disclosed. Specifically, these closures may be used in multiple blood bag systems as disclosed in those applications, or in any other system, where it is desired to provide a removable seal in a flow conduit which may be opened from the exterior of the flow conduit without entry into the interior thereof.

In multiple blood bag systems, the flexible tubing connecting one bag to another is subject to being pulled. For example, a user may hold the multiple bag system by the tubing with the blood bags dangling from the tubing. If the blood bags are filled, this weight may place a substantial stress upon the valve means, urging separation between the outer tubing which the valve means resides in, and the valve means itself.

In accordance with this invention, an improved connection means between the valve means and its outer tubing is provided to assure against separation of the valve components, even when the tubing is yanked. Such separation would of course be expected to render useless the blood bag system or other device containing the valve means.

DESCRIPTION OF THE INVENTION

In this invention, valve means are provided, positioned within a flexible tube. The valve means comprises a tubular portion having a closed end, and an elongated, generally rigid member carried on the exterior of the closed end, and positioned within the flexible tube.

Frangible means are provided to permit the opening of the tubular portion, preferably at the closed end, by rupture of an area of weakness by manual manipulation of the elongated member from outside of the flexible tube.

In accordance with this invention, the flexible tube defines an inner end flange. The tubular end portion of the valve means defines, at its end opposite to the closed end, a retention flange. The retention flange further includes a cylindrical wall positioned generally coaxially to the tube and surrounding the periphery of the inner end flange. The cylindrical wall, in turn, carries an annular closure flange, enclosing and retaining the inner end flange between the closure flange and the retention flange.

As a result of this, the inner end flange of the flexible tube is locked and sealed on all sides by the tubular end portion of the valve means, which significantly increases the resistance of the two components against separation by yanking of the tube or the like.

The inner surface of the inner end flange, which carries an aperture through it, may then be sealed with RF sealing, solvent sealing, or the like to a surface surrounding an aperture in a blood bag, for coaxial sealing of the bore of the tubular end portion and the blood bag aperture together.

The valve means in accordance with this invention may define projecting means on the inner end flange of the tubular end portion, to increase the resistance of the flexible tube to pulling out of the position of retention between the closure flange and the retention flange of the valve means.

The valve means of this invention may be positioned within the flexible tube, and then attached by placing the inner end flange of the flexible tube within an initially cup-shaped flange of thermoplastic material carried at the end of the tubular portion of the valve means, which structure is the precursor to the retention flange, cylindrical wall, and annular closure flange. Then, the lip of the cup-shaped flange may be swaged inwardly to enclose and retain the end flange of the flexible tube, creating the closure flange out of the lip of the cup-shaped flange in the process.

The invention of this application has numerous advantages over the previous designs of frangible valves, for example, as shown in the cited applications. One advantage is that a separate compression flange part may be eliminated. Similarly, the labor required for positioning the separation compression flange onto the frangible valve structure is correspondingly eliminated, which further avoids problems of making defective devices due to assembly error.

Furthermore, the structure of this invention is more susceptible to automated assembly than a three-component design.

Furthermore, as previously stated, the fabricated samples in accordance with this invention exhibit higher horizontal and vertical pull-out values, i.e., it is more difficult to separate the flexible tube and the valve means from each other, than in previous designs. This, in turn, permits rougher handling of the valve means by the user as it is opened, without an increased risk of creating leakage of the seal between the flexible tube and the valve means.

Also, the type of machinery used to fabricate and assemble this present design permits shorter cycle time for automated mass production of improved efficiency.

Preferably, the swaging operation is an ultrasonic swaging technique, utilizing apparatus which is commercially available, for example, an ultrasonic welder with a conical, apertured horn to collapse or reform the cup-shaped flange into the new configuration. Ultrasonic welders made by the Branson Sonic Power Co. of Danbury, Conn. may be used.

Referring to the drawings,

FIG. 1 is a fragmentary elevational view, taken partly in section, of the valve assembly of this invention, sealed to an aperture of a blood bag.

FIG. 2 is a fragmentary, elevational view of the valve means of this invention in its initial form, prior to assembly with the flexible tube and prior to the swaging step.

FIGS. 3, 4 and 5 are enlarged, fragmentary, longitudinal sectional views of alternative modifications of the inner end of the flexible tube utilized herein, to provide added strength to the junction between the flexible tube and the valve means.

Referring to FIG. 1, the valve assembly 10 in accordance with this invention is shown, along with a portion of a multiple blood bag system, including a blood bag 12 and connection tubing 14 which communicates between bag 12 and a transfer pack 16 (shown schematically). Bags 12 and 16 may be of any desired or conventional design.

Valve assembly 18 comprises a flexible tube 17, which may be made of a thermoplastic material such as polyvinyl chloride or a polyolefin material, and valve means 18, which may be made of similar materials. As in the previous embodiments disclosed in the cited applications, valve means 18 may define a tubular portion 20 defining a closing end 22. Elongated, generally rigid member 24 is shown in this particular embodiment to be carried on closed end 22, with frangible means 26 being provided to permit the opening of the tubular portion 20, in this embodiment being positioned at the closed end 22, by rupture of the frangible means 26. Frangible means 26 may comprise an annular line of tearing weakness in closed end 22, as shown.

Accordingly, one may manually grasp generally rigid member 24 through the flexible tube 16 to push it sideways, to tear end wall 22 away from tubular portion 20, to open the flow path through tubular portion 20 and flexible tube 16.

As disclosed in the previously cited Bayham U.S. Application Ser. No. 876,790, the elongated member 24 defines various longitudinal vanes 28, 30 which are of unequal length, with vanes 28 being longer, and preferably sufficiently long to exhibit a perceptible spring-like resilience.

Accordingly, upon manual opening of valve 18 by the bending of generally rigid member 24, to rip open annular weakened area 26, member 24 may be separated and moved backwards by axially collapsible gripping and re-extending flexible tube 16, to be placed into pinching, resilient retention relation between vanes 28 and the conical bore portion 32 of the tube 16. Blood can accordingly flow longitudinally about member 18 between vanes 28, 30, which permits bidirectional flow of fluid as desired through the valve without the danger of rigid member 18 drifting into obstructing relationship again with the bore 34 of tubular portion 20.

If desired, the end of elongated member 18 which defines wall 22 may be proportioned to permit resealing of bore 34 after opening.

The valve assembly 10 is then sealed in conventional manner to a corresponding aperture 36 of blood bag 12, for sterile aseptic sealing of the blood bag, while permitting the institution of a flow relationship through tube 14 by the tearing away of elongated member 24 as described above.

In accordance with this invention, flexible tube 16 defines an inner end flange 38. Correspondingly, the tubular end portion 20 of the valve means 18 defines, at its end opposite to the closed end 22, a retention flange 40, which defines an outer surface, as shown, which may bond to a corresponding flat surface of blood bag 12.

Retention flange 40 further defines a cylindrical wall 42, which is positioned generally coaxially with tube 16, and which surrounds the periphery of the inner end flange 38 of flexible tube 16.

Cylindrical wall 42, in turn, carries an annular closure flange 44, which encloses and retains inner end flange 38 between the closure flange 44 and retention flange 40, for the firm and permanent retention of the two components 16, 18 together.

FIG. 2 shows an intermediate stage of assembly of the valve means 18 of this invention. Basically, retention flange 40 carries a cup-shaped flange 42a, from which flanges 42 and 44 are formed. Flexible tube 17, and particularly its inner end flange 38 are inserted into the cup-shaped flange 42a which forms a cup member with the flange 40. Thereafter, flange 42a, which defines the lip of the cup-shaped member, is swaged inwardly by an insert member 45 which extends into a horn 43 of a sonic welder machine. Insert member 45 has a tapered interior 47, and terminates in apertured wall 54 to form flange 44. Aperture 55 provides room for vanes 28 and related structure during the swaging operation. Thus the configuration of FIG. 1 may be formed, defining cylindrical wall 42 and the closure flange 44 which is formed by the swaging operation, to enclose and retain the end flange 38 of tube 16.

This operation may be performed separately prior to attaching the assembled valve structure 10 to its blood bag 12 by ultrasonic sealing or other means as desired.

Referring to FIGS. 3 through 5, the structure is shown in its semi-finished configuration prior to swaging. In each case retention flange 40 is shown, as well as cup-shaped flange 42a, which is the precursor to the formation of flanges 42 and 44.

Inner end flange 38a of FIG. 3, as part of tubing 16, defines an annular projection 46 in a radially outward area, so that as cup-shaped flange 42a is collapsed by swaging onto it, an irregular gripping surface is provided, to increase the resistance against pulling apart of valve member 18 and tubing 16.

In FIG. 4, inner end flange 38b defines an annular projection 48 pointing outwardly, being adapted to fit in an annular recess 50, which may be defined in retention flange 40 as shown. This also resists pullout between the respective parts after flange 42a is swaged downwardly onto the rear side of flange 38b.

In FIG. 5, flange 38c of tubing 16 defines an intermediately positioned compression ring as shown, against which the swaged flange 42a can impact for added gripping between the respective parts.

Accordingly, an improved breakaway valve is provided which is capable of enduring rougher handling, and which has the manufacturing and other advantages described previously for blood bags and other systems, where easy, aseptic opening of the valves by manipulation from the exterior is desired.

The above has been offered for illustrative purposes only, and is not intended to limit the invention of this application, which is as defined in the claims below.

That which is claimed is:

1. In a valve assembly, a flexible tube, and valve means positioned in said tube, said valve means comprising: a tubular portion having a closed end, an elongated, generally rigid member carried on the exterior of said closed end and positioned within said flexible tube, and frangible means to permit the opening of said tubular portion by rupture of an area of weakness by manual manipulation of the elongated member from outside of the flexible tube, the improvement comprising, in combination, said flexible tube defining an inner end flange, said tubular portion of the valve means defining, at its end opposite to said closed end, a retention flange, said retention flange including a cylindrical wall positioned generally coaxially with said tube and surrounding the periphery of said inner end flange, said cylindrical wall carrying an annular closure flange enclosing and retaining said inner end flange between said closure flange and retention flange.

2. The valve means of claim 1 in which projecting means are defined on said inner end flange to increase the resistance of the flexible tube to pulling out of the position of retention of between said closure flange and said retention flange.

3. The valve means of claim 2 in which said projecting means is an annular projection disposed on said inner end flange and generally coaxially positioned with said flexible tube.

4. The valve means of claim 1 which is part of a multiple blood bag system, and is positioned in flow communication with tubing which communicates between at least a pair of blood bags.

* * * * *